(12) United States Patent
Ebner et al.

(10) Patent No.: US 6,375,663 B1
(45) Date of Patent: *Apr. 23, 2002

(54) BONE GRAFTING MATERIAL

(75) Inventors: Peter R. Ebner; David E. Altobelli, both of Hollis, NH (US)

(73) Assignee: Maxilon Laboratories, Inc., Amherst, NH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,488

(22) Filed: Mar. 17, 1999

(51) Int. Cl.[7] .............................................. A61B 17/32
(52) U.S. Cl. ........................................ 606/170; 623/16
(58) Field of Search .................... 606/80, 167, 170, 606/171, 154, 161, 162, 79, 84; 623/16, 11, 12, 919

(56) References Cited

U.S. PATENT DOCUMENTS

| | | | |
|---|---|---|---|
| 2,526,622 A | 10/1950 | Hipps et al. | 128/92 |
| 3,713,860 A | 1/1973 | Auskern | 117/8.5 |
| 4,366,822 A | 1/1983 | Altshuler | 128/753 |
| 4,535,485 A | 8/1985 | Ashman et al. | 623/16 |
| 4,547,390 A | 10/1985 | Ashman et al. | 427/2 |
| 4,600,005 A * | 7/1986 | Henel | 126/304 |
| 4,643,735 A | 2/1987 | Hayes et al. | 623/16 |
| 4,722,338 A | 2/1988 | Wright et al. | 128/312 |
| 4,728,570 A | 3/1988 | Ashman et al. | 428/327 |
| 4,798,213 A | 1/1989 | Doppelt | 128/754 |
| 4,844,064 A | 7/1989 | Thimsen et al. | 128/305 |
| 4,994,024 A | 2/1991 | Falk | 604/22 |
| 5,133,359 A | 7/1992 | Kedem | 128/754 |
| 5,263,953 A * | 11/1993 | Bagby | 606/61 |
| 5,269,785 A | 12/1993 | Bonutti | 606/80 |
| 5,403,317 A | 4/1995 | Bonutti | 606/60 |
| 5,500,013 A * | 3/1996 | Buscemi et al. | 623/1 |
| 5,650,108 A | 7/1997 | Nies et al. | 264/122 |
| 5,683,406 A * | 11/1997 | Altobelli et al. | 606/170 |
| 5,697,976 A | 12/1997 | Chesterfield et al. | 623/11 |
| 5,919,234 A * | 7/1999 | Lemperle et al. | 623/16 |
| 6,110,177 A * | 8/2000 | Ebner et al. | 606/84 |

OTHER PUBLICATIONS

Product Profile and Corporate Info for Bioplant HTR, Inc.–Date—1974.

The Natural Facts about Pro Osteon 500R Porous Bone graft Substitute—Date—1989.

Henry M. Goldman, Periodonatal Therapy, 1980, 990–1007, St. Louis. Toronto.London.

Patrick C. Haggerty, Autogenous Bone Grafts: A Revolution in the Treatment of Vertical Bone Defects, 1971, 626–641, J. Periodontology.

R. Earl Robinson, Osseous Coagulum for Bone Injection, 1969, 5/503–12/51 J. Periodontology.

Rowland A. Hutchinson, Osseous Coagulum Collection Filter, 1973, 688–690, J. Periodontology.

* cited by examiner

*Primary Examiner*—Allan N. Shoap
*Assistant Examiner*—Lien Ngo
(74) *Attorney, Agent, or Firm*—Hayes Soloway

(57) ABSTRACT

A bone graft material which comprises an expanded volume of a biocompatible material in convoluted form. Typically, the material has a volume increase of at least two fold, preferably five to fifteen fold.

26 Claims, 4 Drawing Sheets

BONE GRAFTING MATERIAL

BACKGROUND OF THE INVENTION

TECHNICAL FIELD

The present invention relates to the field of medicine, and more particularly, to the field of bone grafting. The invention has particular utility in connection with the removal and collection of bone from the surface of one or more donor sites, and the preparation and placement of the autogenous bone material at a second location in the same patient., e.g. for use in grafting bone to osseous deficiencies, such as periodontal and dentoalveolar defects, bone deficiencies around dental implants, and numerous orthopedic applications that require bone grafting, and will be described in connection with such utility, although other utilities are contemplated.

Many reconstructive procedures used in medicine and dentistry involve the manipulation and healing of bones. Such procedures may involve changes in the position, orientation, shape and size of skeletal structures. A problem that is commonly encountered during such procedures is a lack of bone graft material. Bone graft material may be used in many applications, such as to fill between sections of bone that have been repositioned, to change surface geometry, or to add bone to an area that is deficient, such as in conjunction with joint fusion, bone cyst site repair, periodontal surgery or dental implants in a patient's jaw.

Harvesting of small bone grafts from intraoral sites has been a common practice in periodontal surgery to restore bone defects around teeth. In the case of dental implant surgery, bone grafts may be needed to augment atrophic alveolar ridges of the maxilla and/or mandible and the sinus floor to increase the dimension of these bone sites to accommodate and totally cover the endosseous portion of implant fixtures. Bone grafts also are used in conjunction with guided tissue regeneration, a technique that uses a membrane to isolate hard tissue from soft tissue sites and potentiate hard tissue healing.

It is often difficult to harvest adequate amounts of autogenous bone from intraoral sites. Therefore, clinicians often rely on non-autogenous sources of graft material, such as bone from cadaver sources (homologous or allogeneic grafts), animal sources (heterogenous or xenogeneic grafts), or synthetic (alloplastic) bone substitutes. However, healing of non-autogenous material grafts is not as extensive or predictable as healing of autogenous bone obtained directly from the patient; plus the additional cost of such non-autogenous graft materials which can be significant. Autogenous bone is widely known and accepted as the "gold standard."

Clinicians use several techniques to remove bone for grafting for intraoral procedures. In one such technique a rotary instrument, such as a side cutting burr or trephine, is used to remove a piece or section of cortical bone from a local intraoral site in the maxilla or mandible. The cortical bone is often morsalized into a particulate form, either manually with a rongeur like instrument or in a bone mill. The resulting particulate bone is then positioned and packed into the osseous defect around the teeth or implant.

Another technique is to collect bone dust generated by twist drills or taps used to prepare sites for implant placement. Suction devices with filters have been fabricated and manufactured to collect the bone dust from rotary instruments. This bone is then combined with blood to form an osseous coagulum. However, twist drills tend to generate significant heat which causes some necrosis and denatures proteins. While the site may be irrigated to cool the drill bit, much of the bone material may be lost in the irrigating fluid. Saws, burrs and bone mills also may be used for harvesting and/or preparing bone material for grafting; however, the resulting bone material is either quite powdery or block-like particles with pointed or sharp edges with low aspect ratio. Such materials tend to consolidate with minimal porosity. Robinson, R. E. "Osseous Coagulum for Bone Induction", J. Periodontology 40:503(1969). See Hutchinson, R A "Utilization of an Osseous Coagulum Collection Filter", J. Periodontology 44:668(1973). See also Goldman, et al, "Periodontal Therapy", pp 994–1005, C. V. Mosby Co., (1980); and Haggarty, et al., "Autogeneous Bone Grafts: A Revolution in the Treatment of Vertical Bone Defects", J. Periodontology 42:626(1971). While such techniques are widely used by clinicians, such techniques have limitations, since sites for harvesting sections of intraoral bone are limited in number and extent because of limited intraoral access, proximity to tooth roots, nerve structures and sinus cavities, and thin plates of bone.

Surgeons also employ various hand-driven devices such as rasps, reamers, files, rongers, gouges, chisels and osteotomes to cut and harvest bone. However, such hand-held devices are inefficient for harvesting bone for grafting applications, and normally produce powder-like particles. Additionally, harvesting bone using chisels or the like may be hazardous.

When larger amounts of bone are needed for major reconstructive procedures, sites such as the hip (anterior or posterior ilium), tibia, ribs, or the calvarium often are used. However, using such sources necessitates a second surgical site, which may involve more morbidity and require postoperative hospitalization, and thus is less amenable, e.g. in the case of an out-patient dental procedure.

Various surgical devices have been proposed and/or are in use to harvest bone marrow samples for biopsy, or devices such as rongeurs or bone cutters or punches to remove sections or convex edges of bone. Surgical devices also are in use in arthroscopy and endoscopy for cutting or drilling bone or tissue and removing the tissue fragments. Ultrasonic devices also are in use to cut bone; however, such devices require the removal of the irrigant and debris liberated by the apparatus. Each of these methods and/or devices, however, suffers from one or more deficiencies as applied to the collection of bone for grafting.

U.S. Pat. Nos. 5,403,317 and 5,269,785 to Bonutti show a method and apparatus for the percutaneous cutting and removal of tissue fragments from human. The Bonutti device removes the tissue fragments by suction, where it can be collected and then placed elsewhere in the patient from where originally obtained. Bonutti employs a flexible drill, and suction to remove the debris to an externally placed collection reservoir, where it is compressed before being replaced into the patient.

U.S. Pat. No. 2,526,662 to Hipps discloses a bone meal extractor apparatus for mechanically removing bone meal from a donor bone site through a small percutaneous site using a drill. The drill shavings, which comprise primarily sub-surface bone, are then evacuated into an open cut that the drill passes through, for collection.

U.S. Pat. No. 4,798,213 to Doppelt teaches a device for obtaining a bone biopsy for diagnosis of various bone diseases. The Doppelt device is intended to remove a core of bone using a tubular drill, while maintaining the architecture of the tissue. The sample is obtained from the marrow space and not intended for re-implantation.

U.S. Pat. No. 5,133,359 to Kedem shows a hard tissue biopsy instrument in which samples are taken using a rotatably driven hollow needle.

U.S. Pat. No. 4,366,822 to Altshuler discloses a method and apparatus for bone marrow cell separation and analysis. The Altshuler apparatus collects bone marrow cells in a filtration chamber on a filter interposed between a needle directed into the bone marrow site and an aspirator or vacuum source, i.e. using negative pressure to withdrawal marrow cells through a needle.

U.S. Pat. No. 5,052,411 to Schoolman teaches, a vacuum barrier attachment for shielding the operator of a medical tool from harmful aerosols and blood, etc. created by drilling, sawing types of actions, etc. The Schoolman device requires vacuum and is not intended for harvesting tissue for re-implantation.

U.S. Pat. No. 4,722,338 to Wright et al discloses a device instrument for removing bone which uses a shearing action similar to a rongeur to cut bone, with means for collecting fragments of bone as they are removed. The Wright et al device reportedly is used mainly for the removal of projections or edges of bone using a shearing mechanism without the intent of harvesting the bone for grafting.

U.S. Pat. No. 4,994,024 to Falk teaches an arthroscopy hook-clippers device that allows the unobstructed removal of tissue or bone with removal of the fragments by suction. The Falk device is intended for arthroscopy applications and for the removal of projections of tissue or bone and not specifically for the harvest of tissue for grafting.

Yet other prior art devices are disclosed in U.S. Pat. No. 4,466,429 to Loscher et al and U.S. Pat. No. 4,844,064 to Thimsen et al.

In our U.S. Pat. No. 5,683,406, we disclose a hand-held surgical instrument for cutting, removal and storage of bone surface shavings for use as atogenous bone grafts which is an improvement over the aforesaid prior art methods and apparatus. More particularly, as described in our aforesaid parent, there is provided an instrument (which is now available commercially, as the mx-grafter™ bone grafting system from Maxilon Laboratories, Inc., of Hollis, N.H.) comprised of a blade mounted in a handle for holding and supporting the blade. The blade has a cutting structure adjacent its distal end in the form of a sharpened wedge-shaped loop. The loop's wedge shaped cross-section is defined proximally by a perpendicular curved aperture through the blade, and distally by a ground relief. The handle includes a hollow space which provides a storage space adjacent the distal end of the blade for receiving harvested bone from the cutting operation. The instrument is designed to be held at an acute angle to the bone, and with minimal downward pressure, drawn across the bone surface to shave and cut and collect bone material. The blade is retractable to allow the clinician access to the harvested material. A plunger is incorporated into the handle to serve both as a locking mechanism to secure the blade and as a means to advance and consolidate the bone in the distal aspect of the instrument. We have found that the instrument of our aforesaid parent applications, when properly used to cut and harvest bone, creates convoluted shavings or ribbons, filaments or sheets of bone material with blood in its intersities, which material has proved to be uniquely superior for use as bone graft material. Typically, the harvested bone has an expanded volume of at least about two fold, typically five to fifteen fold expanded volume. Also, when harvested from living bone, the harvested convoluted bone material also includes copious quantities of blood with a form similar to the trabeculae of cancellous bone. While not wishing to be bound by theory, it is believed that the cut blood vessels of the bone continue to bleed until exposed to air. Thus, as seen in FIG. 5, the one blood vessel 52A exposed to air is not bleeding, while the other blood vessel 52B continues to bleed into the bone shavings where it is drawn out by a wick-like action into the void spaces 54 subtended by the bone shavings. This latter phenomena is quite unexpected since conventionally cut or drilled bones look quite dry. However, when live bone is shaved, blood from coincidentally cut vessels is drawn into the bone interstices by a wick-like action. The resulting harvested bone material has a substantially increased continuous surface area and occupies a substantially greater volume as compared to the donor bone. The resulting open matrix of convoluted bone shavings allows rapid ingrowth of capillaries and bone growth to take place on the shaving surfaces. This process of healing takes place rapidly compared to that of block or conventionally obtained particulate grafts, because pathways for capillaries exist without the need for significant bone resorption.

Yet other features and advantages of the present invention may become apparent in the following detailed description, taken in conjunction with the accompanying drawings, wherein:

FIG. 1 is a perspective view illustrating a bone harvesting instrument as described in prior U.S. Pat. No. 5,683,406;

DETAILED DESCRIPTION OF PREFERRED EMBODIMENT

Figure 1:
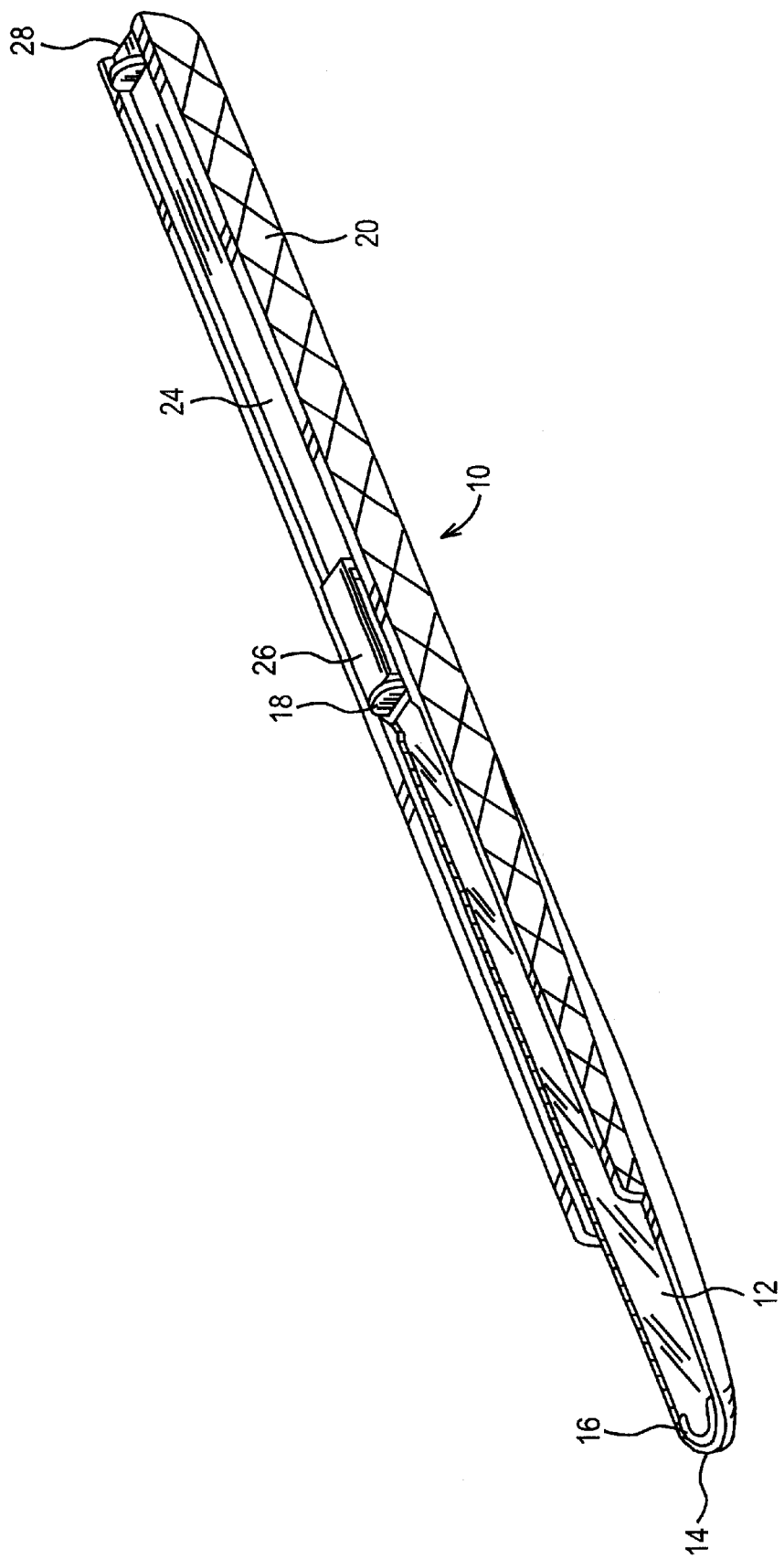
Figure 2:
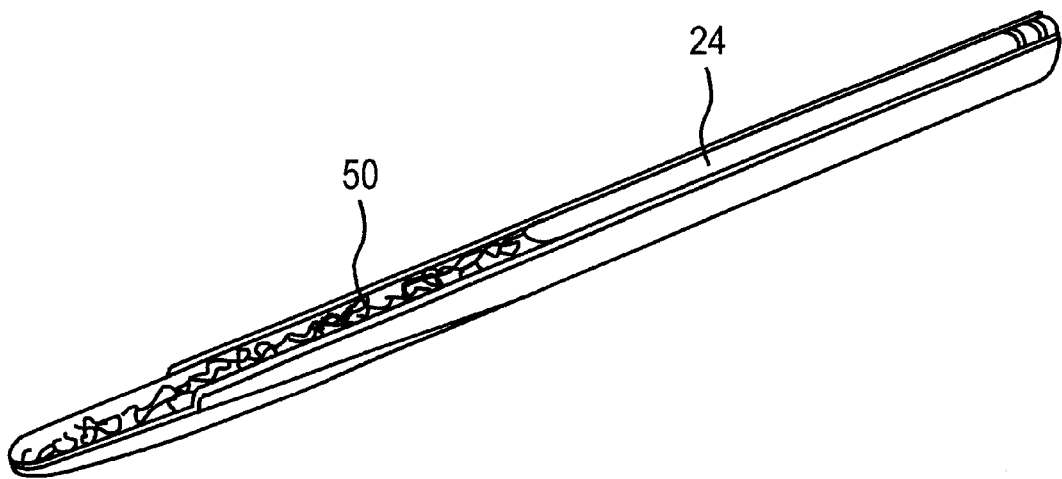
FIG. 2 is a perspective view, with the blade retracted, showing harvested bone in the storage chamber of the instrument of FIG. 1.
Figure 4:
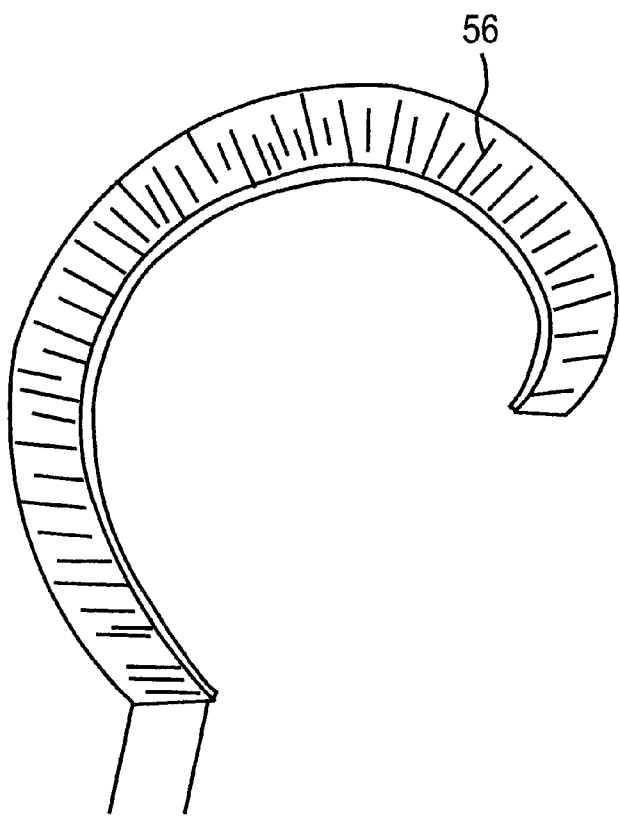
FIG. 4 is a perspective view of a single shaving of convoluted bone material of the present invention.
Figure 3:
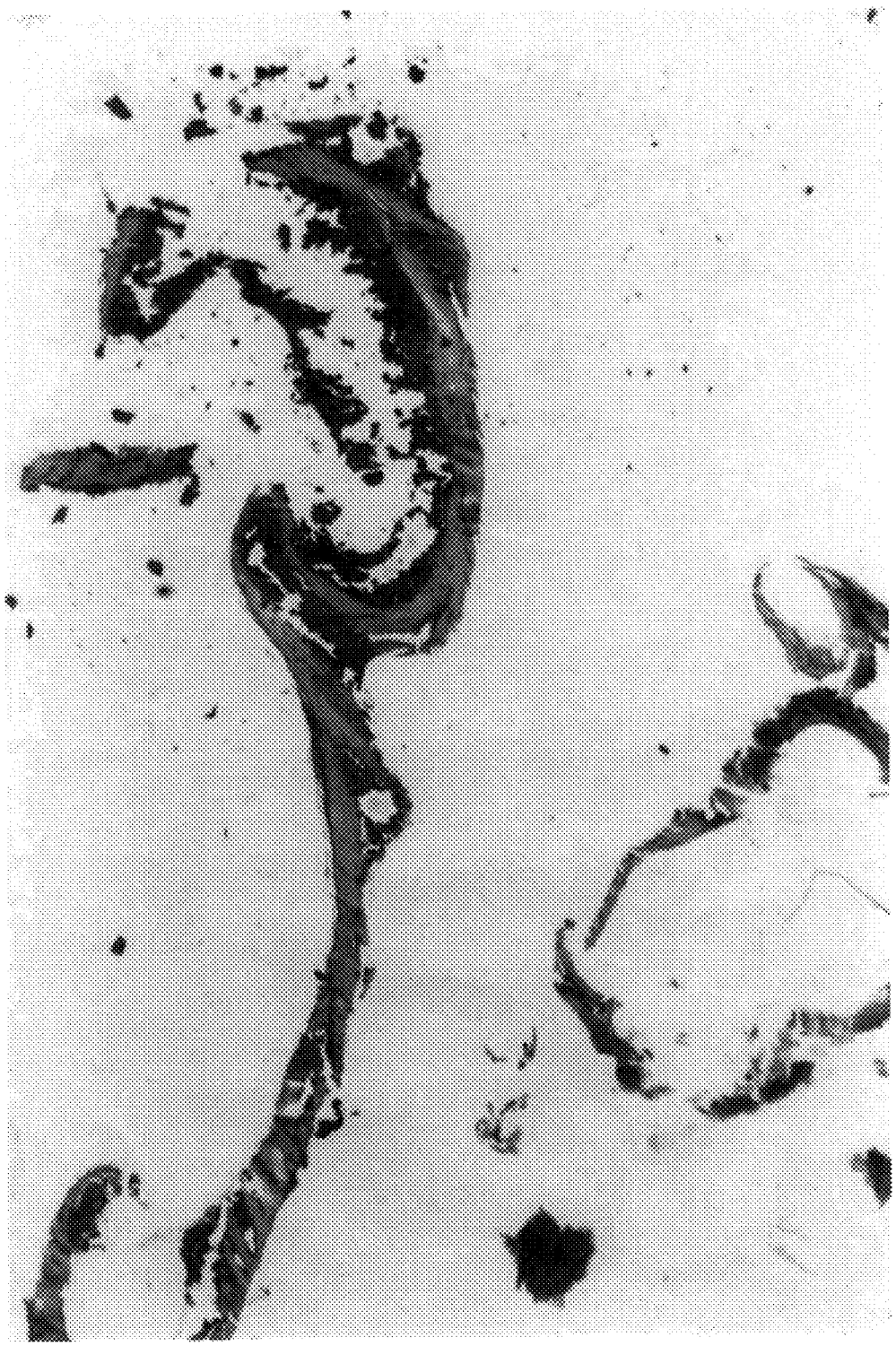
FIG. 3 is a low power photomicrograph of convoluted bone material harvested in accordance with the present invention.
Figure 5:
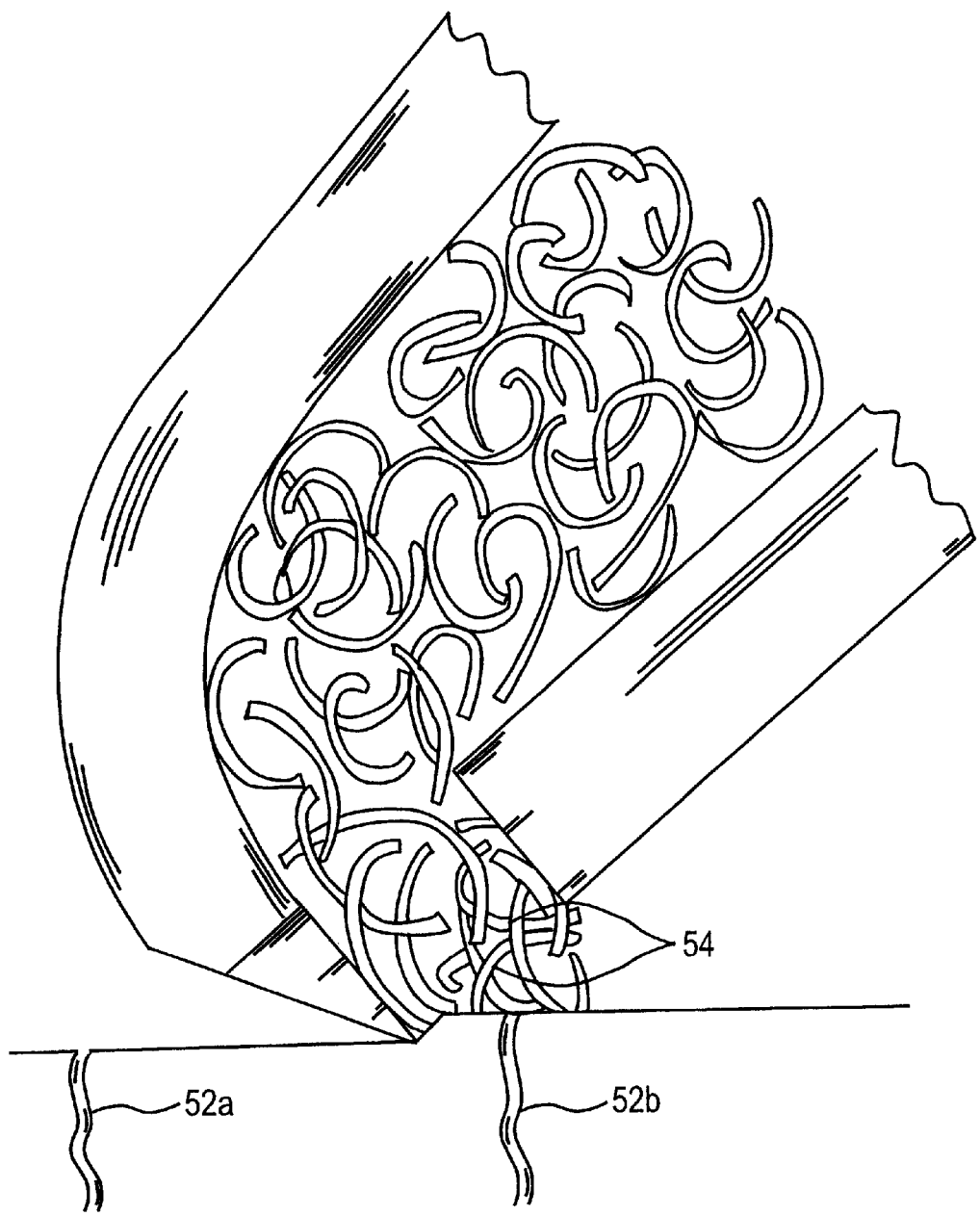
FIG. 5 is a cross-section of bone material being harvested in accordance with the present invention.

Referring to FIGS. 1, 2 and 5, the instrument for harvesting convoluted shavings or ribbons of bone is made in accordance with our aforesaid parent applications, and comprises a blade 12 having a semi-circular cutting edge 14, an aperture 16, a blade tab 18, a handle 20, a plunger 24, a lock button 26 and a plunger tab 28, all as described in greater detail in our aforesaid U.S. Pat. No. 5,683,406, the disclosure of which is incorporated by reference. The back surface of the blade, i.e. the surface away from the one adjacent the bone structure is relieved at 14 between its edges so that the depth of the hole adjacent the cutting edge is equal to or less than the width of the hole 16. This provides easy transfer of elongate shavings or ribbons of shaved bone 50 into the space behind the blade and prevents clogging of the hole during the cutting operation. Referring also to FIGS. 3 and 4, when used in accordance with the teachings of our aforesaid U.S. Pat. No. 5,683,406, the instrument yields convoluted shavings or ribbons of bone having a high surface area to volume, typically about 5–10 mils average thickness, about 30–60 mils average width, and about 75–225 mils average length. Unlike bone material harvested using conventional reamers, drills, saws, etc., the bone material harvested in accordance with the present invention has a significantly greater (two fold or greater) volume as compared to the original bone volume from which the bone was harvested, and a void space of at least about 50 volume percent, typically about 80 to 95 volume percent. This is due to the unique physical structure of the graft material which takes the form of thin convoluted or ribbons, filaments or sheets. This in turn allows a graft material to be easily handled and packed securely in place. Moreover, the convoluted material harvested in accordance with the present invention, in comparison to conventionally harvested bone graft materials, does not have any pointed or sharp edges. This allows the material to be placed securely in position as compared to particulate or chip-like particles. And, without pointed or sharp edges, the graft is more gentle on the flap, and allows the flap to adhere to the graft and minimize tension across the wound closure.

The harvested graft material in accordance with the present invention has other advantages. The graft material, in its physical convoluted form, is significantly more open than conventional bone graft material, and thus promotes rapid ingrowth and revascularization. Moreover, the harvested material includes not only shavings or ribbons, filaments or sheets of bone, but also blood coagulum which further contributes to graft healing.

The harvested bone graft filament or sheet material of the present invention exhibits a wicking action capable of drawing in blood from cut vessels and/or pooled blood, and each shaving has high surface area to volume and a high surface area to mass ratios. Typically, the thickness and width of the shavings or ribbons, filaments or sheets of harvested material is small in comparison to their length. These harvested bone graft shavings or ribbons, filaments or sheets are similar in geometry to shavings or ribbons of material obtained by planing wood. Thus, the shavings or ribbons, filaments or sheets twist and curve in multiple planes and define a volume much greater than their volume (at least two fold, typically five to fifteen or more fold) in the original bulk form of the material. Thus, when multiple shavings or ribbons, filaments or sheets are combined, they interdigitate, and create a matrix-like structure with a highly open volume. We have observed these morphological features have a favorable influence on biological healing response, the volume of bone that needs to be harvested, and the graft's healing characteristics.

The invention has other advantages.

The convoluted ribbons or shavings, filaments or sheets of autogenous cortical bone create a matrix of elements that define a highly open space. Blood fills the interstices of the bone matrix, providing an easily penetrated clot scaffold enabling rapid vascular ingrowth. The blood contains growth factors which stimulate vascular ingrowth and many of the necessary precursors for bone formation. Moreover, the harvested bone is not subjected to elevated temperature during harvesting. Thus, many osteoprogenitor cells survive in the graft material to provide a source of osteoblasts to deposit new bone. Capillaries invade the graft and hematopoietic derived osteoclasts resorb the graft's bone surfaces. Bone morphogenetic proteins are liberated from the graft. These osteoinductive factors can recruit primitive mesenchymal cells that have accompanied the infiltrating vessels to eventually become bone forming cells. With the shaving's or ribbon's high surface area to volume relationship, and high surface area to mass relationship, the open matrix of convoluted shavings or ribbons is analogous to a drug delivery system for these factors in many respects. Furthermore, with the convoluted geometry of the shavings or ribbons, there is at least about a two fold increase in the volume occupied by the random matrix of the harvested bone material in comparison to the volume of the donor bone material.

Prior to growth and differentiation, cells must adhere to and flatten out on a stable surface of sufficient size. Each convoluted element of the present invention, ribbon like in shape, provides continuous surfaces of sufficient dimension to allow numerous cells (approximately 250 to 1,500) to adhere, flatten and spread. Other particulate forms of graft material are often too small to provide adequate continuous surfaces.

Furthermore, surface topography can greatly effect cell shape. Abundant evidence suggests that cell shape can regulate cell growth and differentiation. See, Folkman J. Moscona A., "Role of cell shape in growth control" Nature, 273:345–349, 1978; Watt F M, Jordon P W, O'Neill C H, "Cell shape controls terminal differentiation of human epidermal keratinocytes"; Proc. Natl. Acad. Sci., 85:5576–5580, 1988. The topography of the surface also has an important effect on contact guidance, which refers to the tendency of cells to be guided in their direction of locomotion by the shape of the cell surface. See, Weiss P. Garber B., "Shape and movement of mesenchyme cells as functions of the physical structure of the medium; Contributions of quantitative morphology; Proc. Natl. Acad. Sci. 38:264–280, 1952. Osteoblasts are similarly influenced by contact guidance. See, Brunette D M, Ratkay J. Chebroudi B., "The behavior of osteoblasts on micromachined surfaces", in Bone-Biomaterial Interface, J. E. Daves (ed.), Univ. of Toronto Press, pp. 170–180 1991. Effective surface feature grooves are on the order of 1.6–30 microns wide and 3 microns deep. See, Chehroudi B. Brunette D M, "Effects of Surface Topography on Cell Behavior," in "Encyclopedic Handbook of Biomaterials and Bioengineering" edited by Wise D L, Trantolo D J, Altobelli D A, Yaszemski M J, Gresser J D, Schwartz E R. Marcel Dekker, Inc. New York 1995. Part A, Vol. 1, Chap. 22, pp. 813–842.

The present invention's convoluted elements have a favorable textured topography. In addition to the natural topography provided by the bone's fibrous stroma and the lucunae depressions, the cutting process also introduces a textured surface topography 56.

The dominant topographic features are predominantly perpendicular to the long axis of the element, caused largely by the chip breaking effect of the blade during cutting. More subtle features can also run predominately parallel to the long axis of the element and are caused by features or irregularities in the edge of the cutting tool.

The perpendicular features may be in the form of protuberances on the concave side of the convoluted element and depressions on the element's convexity, whereas longitudinal features such as lines or grooves may be caused by irregularities in the edge of the cutting tool. The morphology of these features can vary greatly depending on the orientation of the bone lamellae during the cutting process.

When bone-grafting procedures are performed, it is usually necessary to generate a graft shape that is a replica of the natural shape that would normally be present at the site. The graft material of the present invention, convoluted bone shavings and blood, offers several distinct benefits in its ability to be easily modeled and then retain its shape during surgery, immediately after surgery and throughout the healing process. Its ability to be modeled allows for more accurate restoration of osseous features and often eliminates the need for costly and complex shape defining meshes or other functionally similar structures.

High aspect ratio convoluted bone shavings, when mixed with blood, form a graft material, that shapes like mortar or modeling clay. Conventional particulate bone and blood graft material does not hold its shape well, and tends to fall apart into small clumps when handled, or if modeling is attempted. The advantage, in this regard, of the material of the present invention is due to the much greater surface area of each of the high aspect ratio convoluted shavings which blood can adhere to and bond together. Also contributing to the convoluted graft's cohesiveness is the entanglement of the convoluted shavings with one another. These interactions add significant geometrical stability to the graft in the presence of various random and systemic loads, intra-operatively and post-surgically. With conventional, low aspect ratio particulate graft material, relatively small loads cause the bonds to fail, because blood can only adhere to the relatively small amount of surface area of each particle and the particles cannot become entangled with one another.

The material of the present invention initially has a consistency that makes it easy to handle, form, and then retain shape intra-operatively. Additionally, the material maintains its shape in the post-surgical phase prior to and during healing. Blood platelets adhere to the large continuous surface area of exposed collagen on the convoluted elements. This initiates the formation of a blood coagulum that serves to "glue" the convoluted elements together into a stable composite matrix. A short time later, cross-linking of the fibrin clot renders a firm block-like consistency. The clotting process can be accelerated by the application of an agent such as Thrombin at the appropriate time. The agent may be either mixed with the graft material or coated over the graft after it is in place and shaped. As healing progresses, bone shaving to shaving contact sites fuse early and assume the loads as the blood clot undergoes resorption.

Convoluted bone shavings and blood is a composite material that is structurally similar to fiberglass/epoxy-resin systems. The bone shavings are analogous to the glass fibers and the blood is analogous to the epoxy-resin adhesive. Although the blood clot's strength alone is minimal, when combined with convoluted bone shavings, the composite material has significantly greater strength. Both composite systems (fiberglass/epoxy-resin and convoluted bone and blood) utilize high strength, high modulus, high aspect ratio elements and a low strength low modulus adhesive material. These composite systems gain high bulk strength and rigidity because high aspect ratio elements enable loads to be applied over their extended lengths thereby affording ample surface area for the relatively low strength adhesives to be effective. Unlike bone graft material in the form of low aspect ratio particles with a low surface area per particle, the more fiber-like convoluted elements of the present invention present a high surface area per element, forming a much stronger composite.

In its clotted form, the material of the present invention provides the microscopic structural stability which is necessary for normal bone growth and remolding, and to reduce the risk of scar tissue formation. On a microscopic level, spherically shaped cells need to attach to surfaces to allow them to flatten and spread. The cells tend to be spherical in form largely because of their hydrophobic lipid membranes and their presence in an aqueous environment. For the cells to attach to a surface and redistribute their volume in a more flattened, higher surface area form, the substratum must have adequate rigidity to resist the tendency for the cell to return to a more spherical shape. Unlike low aspect ratio particulate graft material, convoluted bone and blood graft material provides large geometrically stable surfaces on which multiple cells (approximately 250 to 1,500) can undergo the necessary adherence, flattening and spreading prior to growth and differentiation.

In addition, the convoluted bone-blood composite material, when firmly placed into the defect site, forms a stable, matte-like surface without the protruding sharp or pointed edges typical with particulate forms of bone grafts. The convoluted surface of the bone graft material of the present invention has been found to be gentle to the flap soft tissues that overlay a graft site with a natural adhesion occurring between the graft and the soft tissue. This effect is usually seen with the fibrin elements in the blood clot that provide an adhesive like function to stabilize tissues at a wound site. When the flap is gently stretched over the graft to re-approximate the wound edges, this adhesive effect stabilizes the soft-tissue flap over its entire underlying surface which helps greatly to take the tension off the tissue closure at the wound edge. Increased tension in the sutures and the tissues the sutures engage reduces blood flow to the peripheral boundaries of the flap. This can lead to necrosis of the tissue and dihiscence or separation over the wound edges with increased change of infection at this site.

Yet other advantages of the present invention include:
(1) Much less donor sight morbidity because much less bone needs to be taken due to material volume expansion;
(2) Rapid healing enables patient to return to normal life sooner; earlier placement of dental implants;
(3) Biological advantages offer more predictable healing and less complications;
(4) Much lower cost when hospitalization is avoided;
(5) Lower cost because enhanced healing greatly reduces the need for barrier membranes; and
(6) Bone may be taken from the recipient site, molded and returned to that site, thus eliminating the need for a second surgical site.

While the foregoing invention has been described in connection with the use of our patented surgical instrument for cutting and collecting autogenous bone graft material, it will be appreciated that the invention also advantageously may be employed in connection with allogeneic bone graft material, xenogeneic bone graft material and alloplastic bone graft material. Also, other devices capable of cutting and collecting bone material in the form of convoluted shavings or ribbons, filaments or sheets may be employed for creating bone graft material comprising an expanded volume of biocompatible material in convoluted form in accordance with the present invention.

What is claimed is:

1. A bone graft material comprising an expanded volume of natural bone shavings in convoluted form comprising multiple planes, and including autogenous blood coagulum, morphogentic factors and/or recombinant growth factors interspersed therein, wherein said bone shavings have a textured surface topography, and comprise at least about a two fold expanded volume over the natural bone.

2. The material of claim 1, wherein said bone shavings have a five to fifteen fold expanded volume over the natural bone.

3. The material of claim 1, wherein said bone shavings are in the form of elongated ribbons, filaments or sheets.

4. The material of claim 1, wherein said bone comprises allogeneic bone.

5. The material of claim 1, wherein said bone comprises xenogeneic bone.

6. The material of claim 1, wherein said bone comprises autogenous bone.

7. The material of claim 1, wherein said bone comprises alloplastic bone.

8. The material of claim 1, wherein the expanded volume subsumes a void space of at least about 50 volume percent.

9. The material of claim 8, wherein the expanded volume subsumes a void space of about 80 to about 95 volume percent.

10. The material of claim 1, wherein said shavings have an average thickness in the range of about 5–10 mils.

11. The material of claim 1, wherein said shavings have an average width of about 30–60 mils.

12. The material of claim 1, wherein the shavings have an average length of about 75–225 mils.

13. The material of claim 3, wherein said shavings exhibit a wicking action capable of drawing in blood.

14. A moldable bone graft material comprising an expanded volume of natural bone shavings in convoluted form comprising multiple planes, and including autogenous blood coagulum, morphogentic factors and/or recombinant growth factors interspersed therein, wherein said bone shavings have a textured surface topography, and comprise at least about a two fold expanded volume over the natural bone.

15. The material of claim 14, wherein said bone shavings have a five to fifteen fold expanded volume.

16. The material of claim 14, wherein said bone shavings are in the form of elongated ribbons, filaments or sheets.

17. The material of claim 1, wherein said bone comprises allogeneic bone.

18. The material of claim 14, wherein said bone comprises xenogeneic bone.

19. The material of claim 14, wherein said bone comprises autogenous bone.

20. The material of claim 14, wherein said bone comprises alloplastic bone.

21. The material of claim 14, wherein the expanded volume subsumes a void space of at least about 50 volume percent.

22. The material of claim 21, wherein the expanded volume subsumes a void space of about 80 to about 95 volume percent.

23. The material of claim 14, wherein said shavings have an average thickness in the range of about 5–10 mils.

24. The material of claim 14, wherein said shavings have an average width of about 30–60 mils.

25. The material of claim 14, wherein the shavings have an average length of about 75–225 mils.

26. The material of claim 16, wherein said shavings exhibit a wicking action capable of drawing in blood.

* * * * *